US00PP30217P2

(12) United States Plant Patent
de Ruyver

(10) Patent No.: US PP30,217 P2
(45) Date of Patent: Feb. 19, 2019

(54) JERUSALEM CHERRY PLANT NAMED 'RUYSOP1703'

(50) Latin Name: ***Solanum pseudocapsicum* L.**
Varietal Denomination: RUYSOP1703

(71) Applicant: Kurt de Ruyver, Oudenaarde (BE)

(72) Inventor: Kurt de Ruyver, Oudenaarde (BE)

( * ) Notice: Subject to any disclaimer, the term of this patent is extended or adjusted under 35 U.S.C. 154(b) by 0 days.

(21) Appl. No.: 15/732,104

(22) Filed: Sep. 19, 2017

(51) Int. Cl.
*A01H 5/08* (2018.01)

(52) U.S. Cl.
USPC ..... Plt./258

(58) Field of Classification Search
USPC ..... Plt./258, 261
CPC ... A01H 5/08; A01H 5/12; A01H 5/00; A01H 6/82; A01H 5/02; A01H 5/06; A01H 6/85
See application file for complete search history.

(56) References Cited

PUBLICATIONS

Facebook Stekbedrijf Bergs as attending Plantarium 2016, retrieved on Aug. 8, 2018, retrieved from the Internet at https://www.facebook.com/bergsnl/photos/a.346050452148137.85063.345366015549914/1127343207352187/?type=3&link_share, one page. (Year: 2016).*

Google English translation, https://translate.google.com/#auto/en/We%20introduceren%20op%20Plantarium%20onze%20nieuwe%20Solanum%20Per%20Luna%C2%AE%20geschikt%20voor%20kleine%20pot%2C%20genetisch%20compact%2C%20witte%20bes%20die%20naar%20donker%20oranje%20verkleurd.%20Welkom%20in%20stand%20nr%20137,1p. (Year: 2018).*

Floragard for Jerusalem Cherry 'Jupiter' retrieved on Aug. 8, 2018, retrieved from the Internet at https://www.floragard.de/en/Pflanzeninfothek/Pflanzen/251484_Jerusalem+cherry/, 4 pp. (Year: 2018).*

Plantica *Solanum pseudocapsicum* 'Blushberry' retrieved on Aug. 8, 2018, retrieved from the Internet at https://www.plantica.cz/en/indoor-flowers/solanum-pseudocapsicum-blushberry.html, 2 pp. (Year: 2018).*

Stekbedrijf Bergs News Google English translation, retrieved on Aug. 8, 2018, retrieved from the Internet at https://translate.google.com/translate?hl=en&sl=nl&u=http://www.bergs.nl/nl/nieuws/introductie-witbonte-solanum-op-ipm-2018&prev=search, one page. (Year: 2018).*

* cited by examiner

*Primary Examiner* — June Hwu
(74) *Attorney, Agent, or Firm* — Samuel R. McCoy, Jr.

(57) ABSTRACT

A new and distinct *Solanum pseudocapsicum* cultivar named 'RUYSOP1703' which is characterized by the combination of a slow rate of growth, a compact flattened globular plant form with outward facing lateral branches, variegated foliage with dark green centers and broad light yellow margins, immature berries which are white and striped green, small orange-red mature berries, and the stability of these characteristics from generation to generation.

4 Drawing Sheets

Latin name of the genus and species: The Latin name of the genus and species of the novel variety disclosed herein is *Solanum pseudocapsicum* L.

Variety denomination: The inventive cultivar of *Solanum* disclosed herein has been given the variety denomination 'RUYSOP1703'.

BACKGROUND OF THE INVENTION

Parentage: 'RUYSOP1703' originated as a branch mutation from a *Solanum pseudocapsicum* 'Jupiter' (not patented) which was discovered at a commercial greenhouse in Oudenaarde, Belgium. In May of 2016, the inventor discovered a variegated branch mutation growing from a 'Jupiter' seedling. Several cuttings were harvested from the mutated branch and rooted for further evaluation in order to confirm the distinctness and stability of the characteristics first observed. Upon confirmation of distinctness and stability, 'RUYSOP1703' was selected for commercialization in July of 2016.

Asexual Reproduction: Asexual reproduction of 'RUYSOP1703', by way of softwood stem cuttings, was first performed in January of 2017 in Heythuysen, Netherlands. Through two subsequent generations, the unique features of this cultivar have proven to be stable and true to type.

SUMMARY OF THE INVENTION

The cultivar 'RUYSOP1703' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'RUYSOP1703'. These characteristics in combination distinguish 'RUYSOP1703' as a new and distinct *Solanum* hybrid cultivar:

1. *Solanum* 'RUYSOP1703' exhibits a slow rate of growth with a compact, flattened globular plant form and outward facing lateral branches; and
2. *Solanum* 'RUYSOP1703' exhibits variegated foliage with dark green centers and light yellow broad, irregular margins; and
3. *Solanum* 'RUYSOP1703' exhibits immature berries which are white and striped green; and 4. *Solanum* 'RUYSOP1703' exhibits small orange-red mature berries.

BOTANICAL DESCRIPTION OF THE PLANT

Figure 1:
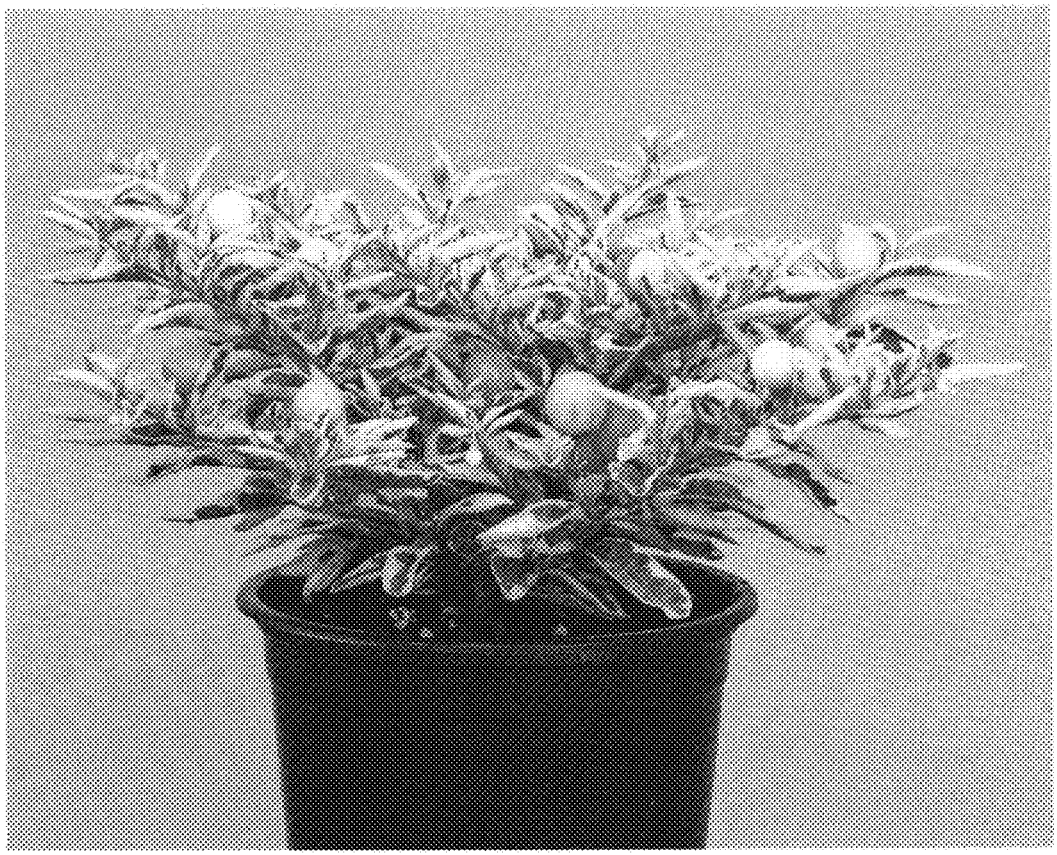
FIG. 1 illustrates, as nearly true as it is reasonably possible to make the same in color photographs of this type, an exemplary 14 week old 'RUYSOP1703' plant, field-grown in Oudenaarde, Belgium.
Figure 2:
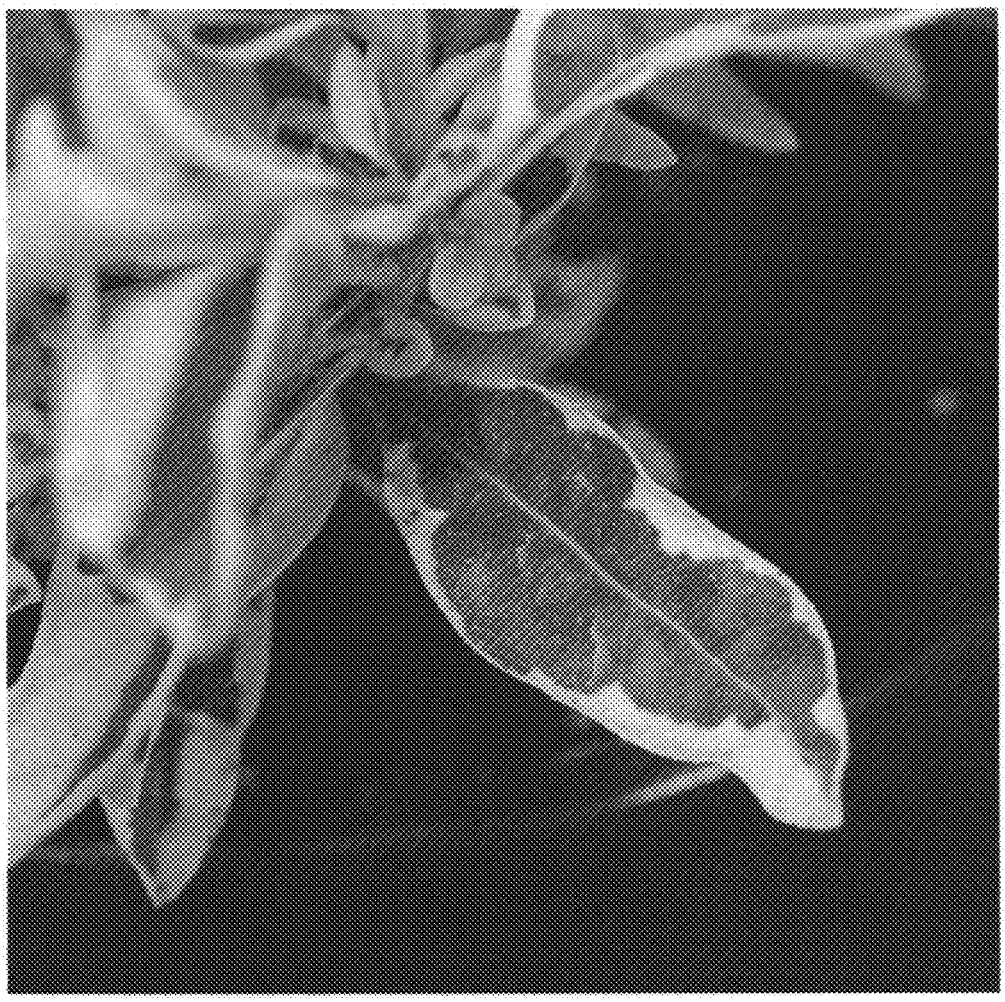
FIG. 2 illustrates, as nearly true as it is reasonably possible to make the same in color photographs of this type, the typical foliage of 'RUYSOP1703'.
Figure 3:
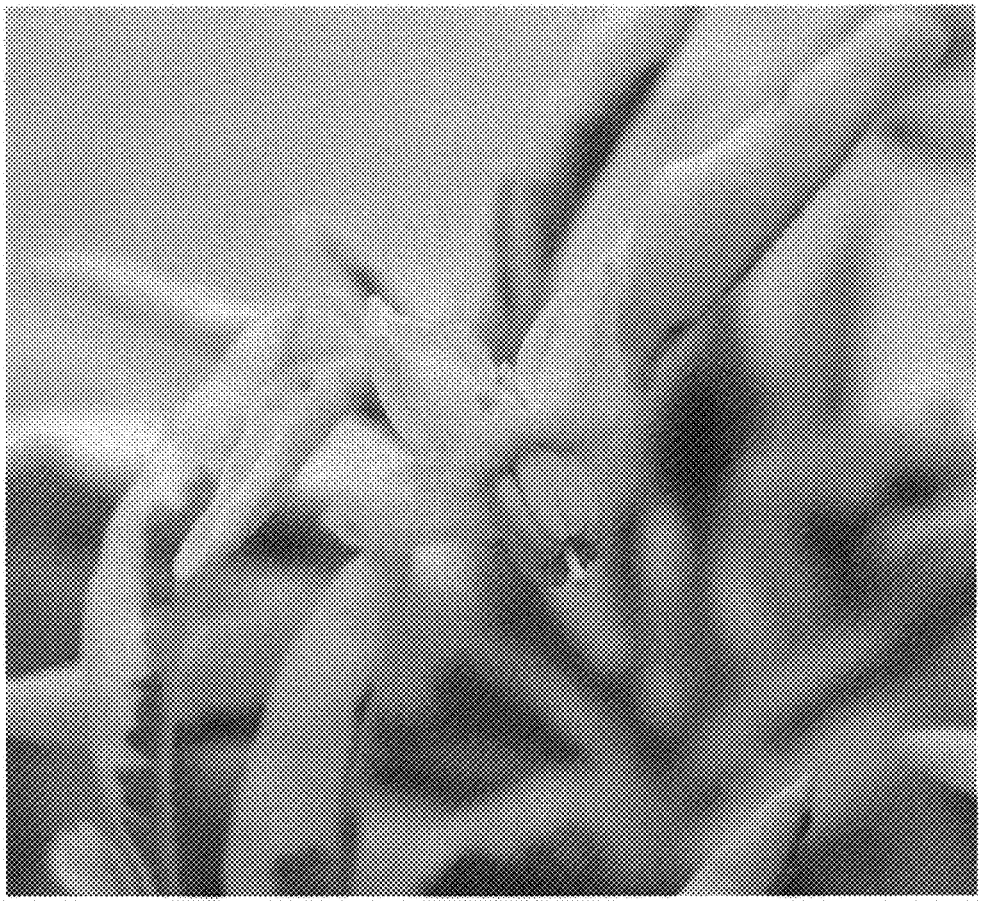
FIG. 3 illustrates, as nearly true as it is reasonably possible to make the same in color photographs of this type, the typical flower of 'RUYSOP1703'.
Figure 4:
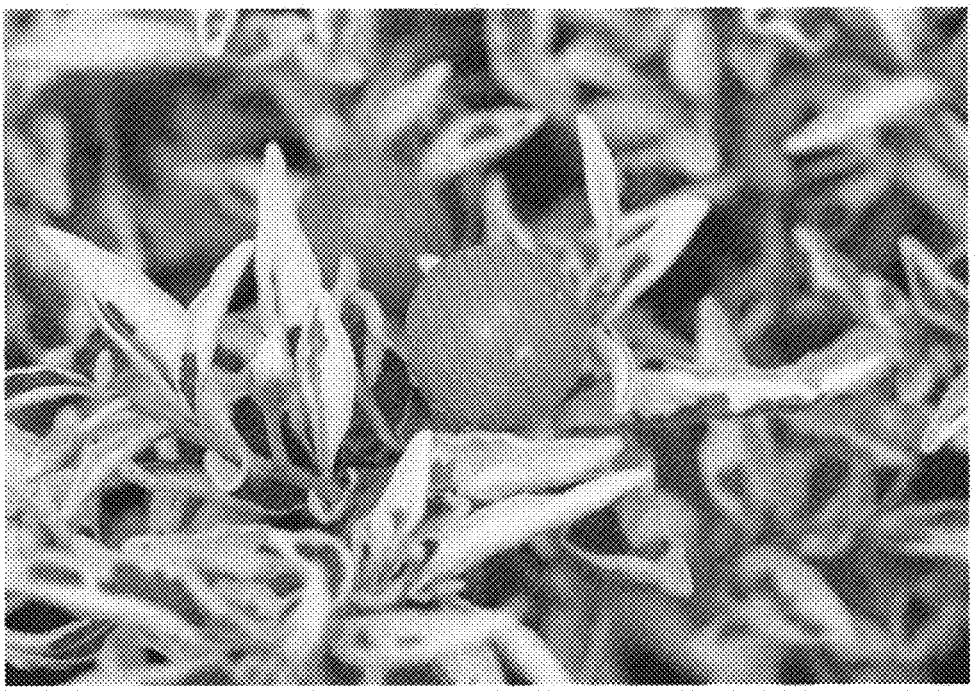
FIG. 4 illustrates, as nearly true as it is reasonably possible to make the same in color photographs of this type, the typical fruit of 'RUYSOP1703'.

The following is a detailed botanical description of a new and distinct variety of *Solanum* known as 'RUYSOP1703', based upon observations of 14 week old field-grown plants in 13 cm nursery containers, produced in Oudenaarde, Belgium. Plants were grown using conventional production protocols for *Solanum* plants which consisted of overhead irrigation, as well as fertigation applications. No pest or disease control measures were utilized in production. Plants were produced with full sun exposure and no photoperiodic treatments or artificial light was given to the plants. Observation data was recorded in August of 2017.

Those skilled in the art will appreciate that certain characteristics will vary with older or, conversely, with younger plants. 'RUYSOP1703' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 edition.

A botanical description of 'RUYSOP1703' and a comparison with the parent plant and the most similar commercial *Solanum* cultivar known to the inventor, is provided below.

Plant description:

*Growth habit*.—Broad, spreading perennial.

*Plant form*.—Compact, flattened globular.

*Average height*.—10.7 cm.

*Average width*.—26.7 cm.

*Plant vigor*.—Low to moderately vigorous.

*Rate of growth*.—Slow.

*Propagation details*.—Asexual propagation may be accomplished by both softwood stem cuttings.

*Time to initiate roots*.—Rooting is initiated in approximately 15 days when grown in with an ambient average temperature of 18 degrees Celsius.

*Time to produce a marketable finished plant*.—Approximately 16 weeks from a rooted cutting.

*Pest resistance and susceptibility*.—Not any more or less tolerant or susceptible to pests or diseases known to effect *Solanum pseudocapsicum*.

*Environmental tolerances*.—Adapt to USDA Zones 10 to 13 and temperatures ranging from at least 5 degrees Celsius to 45 degrees Celsius; moderate tolerance to rain; low to moderate tolerance to wind.

Root system: Dense fibrous root system; relatively shallow distribution in the soil profile.

Stems:

*Branching habit*.—Basally branching main stems; freely branching with lateral branches. Stems and branches are aromatic when touched, typical of *Solanum*. Pinching isn't required but may improve branching.

*Main stem*.—Quantity — 6. Length — 12.8 cm. Diameter — 0.2 cm. Internode length — 0.5 cm. Color — Yellow-green, nearest to RHS 144B. Texture — Covered with short, glandular pubescence; hairs are colored green-white, nearest to RHS 157D, with an average length of 0.3 cm. Luster — Very slightly glossy.

*Lateral branches*.—Quantity — 34. Aspect — Outward; at an approximate angle of 30 degrees from horizontal. Shape — Rounded. Strength — Moderately strong. Texture — Covered with short, glandular pubescence; hairs are colored green-white, nearest to RHS 157D, with an average length of 0.3 cm. Luster — Very slightly glossy. Color of developing branches — Yellow-green, nearest to RHS 144D. Color of mature branches — Yellow-green, nearest to RHS 144B. Color at internodes — Yellow-green, nearest to RHS 144B.

Foliage:

*Arrangement*.—Alternate.

*Attachment*.—Sessile.

*Division*.—Simple.

*Number of leaves on lateral branches*.—26 on average.

*Lamina*.—Dimensions — 4.0 cm long and 1.5 cm wide, on average. Thickness — Approximately 1 mm at the midrib. Shape — Irregular ovate to near elliptic. Aspect — Slightly convex. Apex — Acute. Base — Attenuate. Margin — Entire to irregularly angulate; slightly undulated. Texture adaxial surface — Strongly rugose and densely covered with very short, glandular pubescence; average length of hairs is 0.02 cm and colored green-white; hairs are so minute that it is impossible to accurately assign an R.H.S. color designation. Luster of adaxial surface — Matte. Texture abaxial surface — Strongly rugose and densely covered with very short, glandular pubescence; average length of hairs is 0.02 cm and colored green-white; hairs are so minute that it is impossible to accurately assign an R.H.S. color designation. Luster of abaxial surface — Matte. Color — Juvenile foliage, adaxial surface — Yellow-green, nearest to RHS 150D, with an irregular greyed-green central blotch, nearest to RHS 191A. Juvenile foliage, abaxial surface — Yellow-green, nearest to RHS 150C, with an irregular yellow-green central blotch, nearest to RHS 148B. Mature foliage, adaxial surface — Greyed-green, nearest to a combination of RHS 189A and N189C, and irregularly margined green-yellow, nearest to RHS 1D. Mature foliage, abaxial surface — Greyed-green, nearest to RHS 189A, and irregularly margined yellow-green, nearest to RHS 150C. Venation — Pattern — Pinnate. Color, adaxial surface — The midrib and primary veins are green-yellow, nearest to RHS 1D; secondary and tertiary veins are green, nearest to RHS 147D. Color, abaxial surface — The midrib and primary veins are yellow-green, nearest to RHS 150C; secondary and tertiary veins are yellow-green, nearest to a combination of RHS144A and 144B.

*Petiole*.—None; leaves are sessile.

Inflorescence:

*Type*.—Flowers are solitary or in pairs and placed axially.

*Natural flowering season*.—From late spring through late winter into late autumn in Oudenaarde, Belgium.

*Flowering habit*.—Continuous; moderately floriferous.

*Quantity of open flowers per plant*.—Approximately 8.

*Quantity of buds per plants*.—Approximately 22.

Flower buds:

*Shape*.—Ovate.

*Length*.—Average of 0.6 cm.

*Diameter*.—Average of 0.3 cm.

*Texture*.—Sparsely covered with short, glandular pubescence; average length of hairs is 0.02 cm and colored white; hairs are so minute that it is impossible to accurately assign an R.H.S. color designation.

*Luster*.—Matte.

*Color*.—Yellow-green, nearest to in between RHS 150D and 155A; the proximal portion comprising the immature calyx is green, nearest to RHS 138C.

Flower:

*Form*.—Rotate; single.

*Flower vertical height*.—1.0 cm.

*Flower diameter*.—1.2 cm.

*Flower length*.—0.7 cm.

*Aspect*.—Flowers are nodding.

*Fragrance*.—Non-fragrant.

*Lastingness*.—Approximately 5 days.

*Persistent*.—Self-cleaning.

*Pedicels*.—Dimensions — 0.5 cm long and 0.01 cm in diameter. Aspect — Upward; approximately 40 degrees to the peduncle axis. Strength — Moderately strong. Texture — Smooth; glabrous. Luster — Matte. Color — Yellow-green, nearest to RHS 147D.

*Petals*.—Quantity of Petals — 5. Arrangement — Rotate; fused at the base. Shape — Ovate to near deltoid. Dimensions — 0.55 cm long and 0.3 cm wide. Apex — Acute. Base — Fused. Margin — Entire; not undulated. Aspect — Strongly reflexed. Texture and luster of upper surface — Slightly velvety; matte. Texture and luster of lower surface — Slightly velvety; very slightly glossy. Petal color when opening, upper surface — White, nearest to RHS NN155B. Petal color when opening, lower surface — White, nearest to RHS NN155B. Petal color when fully opened, upper surface — White, nearest to RHS NN155B and fading to NN155D. Petal color when fully opened, lower surface — White, nearest to RHS NN155B and fading to NN155D. Petal venation color, fully opened, upper surface — White, nearest to RHS NN155B. Petal venation color, fully opened, lower surface — White, nearest to RHS NN155B.

*Calyx*.—Shape — Rotate. Length — 0.2 cm. Diameter — 0.6 cm. Sepals — Arrangement — Rotate; fused at the base. Quantity — 5. Length — 0.2 cm. Width — 0.15 cm. Shape — Ovate to near deltoid. Apex — Acute. Base — Fused. Sepal lobe margin — Entire; not undulated. Texture and luster, upper surface — Glabrous, smooth; matte. Texture and luster, lower surface — Glabrous, smooth; matte. Color when opening, upper surface — Nearest to in between yellow-green, RHS 150D, and white, RHS 155A, with a very narrow light green central blotch; blotch is so minute that it is impossible to accurately assign an R.H.S. color designation. Color when opening, lower surface — Yellow-white, nearest to RHS 158D. Color when fully opened, upper surface — Nearest to in between yellow-green, RHS 150D, and white, RHS 155A, with a very narrow light green central blotch; blotch is so minute that it is impossible to accurately assign an R.H.S. color designation. Color when fully opened, lower surface — Yellow-white, nearest to RHS 158D.

Reproductive organs:

*Stamens*.—Quantity — 5. Anthers — Attachment — Basifixed. Shape — Narrow oblong; comprised of 2 anther sacs. Dimensions — Approximately 0.25 cm and 0.1 cm. Color — Yellow-orange, nearest to RHS 23A. Filaments — Length — Approximately 0.1 cm. Color — Yellow-green, nearest to RHS 145C. Pollen, amount — Low. Pollen color — White, nearest to RHS 155A.

*Pistil*.—Quantity — 1. Length — 0.325 cm. Style — Length — 0.3 cm. Color — Green-white, nearest to RHS 157D. Stigma — Shape — Club-shaped. Length — 0.025 cm. Diameter — 0.025 cm. Color — Yellow-green, nearest to RHS 144B. Ovary Color — Yellow-green, nearest to RHS 144A.

Seed and fruit:

*Fruit*.—Type — Berry; non edible. Quantity — An average of 20 per plant. Dimensions — 1.3 cm long and 1.3 cm in diameter. Length — 23 mm, on average. Shape — Spherical. Texture and luster — Smooth, glabrous and glossy. Color, immature — Nearest to in between green-white, RHS 157C, and white, RHS 155C; irregularly striped yellow-green, nearest to RHS 144C. Color, developing fruit — Yellow-orange, nearest to a combination of RHS 15A and 15B. Color, mature fruit — Orange-red, nearest to a combination of RHS N30B and N30C. Color of the mature flesh — Orange-red, nearest to RHS N30B.

*Seed*.—Quantity of seed per fruit — 24. Shape — Flattened; outline is ovate to globular. Length — 0.3 cm. Width — 0.2 cm. Texture — Smooth. Color — Greyed-yellow, nearest to RHS 161C.

COMPARISON WITH THE PARENT

Plants of the new cultivar 'RUYSOP1703' may be distinguished from its parent, *Solanum pseudocapsicum* 'Jupiter' (not patented), by the characteristics described in Table 1.

TABLE 1

| Characteristic | 'RUYSOP1703' | 'Jupiter' |
|---|---|---|
| Rate of growth. | Faster than 'Jupiter'. | Slower than 'RUYSOP1703'. |
| Growth habit. | Broad, spreading. | Upright. |
| Presence of leaf variegation. | Present. | Absent. |

COMPARISON WITH THE CLOSEST KNOWN COMMERCIAL COMPARATOR

Plants of the new cultivar 'RUYSOP1703' may be distinguished from the most similar known commercial comparator, *Solanum pseudocapsicum* 'Ivema' (not patented), by the characteristics described in Table 2.

TABLE 2

| Characteristic | 'RUYSOP1703' | 'Ivema' |
|---|---|---|
| Rate of growth. | Slower than 'Ivema'. | Faster than 'RUYSOP1703'. |
| Growth habit. | More upright than 'Ivema'. | Less upright than 'RUYSPO1703'. |
| Leaf size. | Smaller than 'Ivema'. | Larger than 'RUYSOP1703'. |
| General coloration of the foliage. | Variegated; broadly margined light yellow. | Variegated; narrowly margined with light yellow. |
| Size of the fruit. | Smaller than 'Ivema'. | Larger than 'RUYSOP1703'. |

That which is claimed is:

1. A new and distinct cultivar of *Solanum* plant named 'RUYSOP1703', substantially as described and illustrated herein.

* * * * *